(12) United States Patent
Khosrovaninejad

(10) Patent No.: US 9,339,272 B2
(45) Date of Patent: May 17, 2016

(54) SURGICAL DEVICE FOR THE TEMPORARY PROTECTION OF ANASTOMOSIS

(76) Inventor: Charam Khosrovaninejad, Pernes les Fontaines (FR)

(*) Notice: Subject to any disclaimer, the term of this patent is extended or adjusted under 35 U.S.C. 154(b) by 834 days.

(21) Appl. No.: 13/147,199

(22) PCT Filed: Feb. 9, 2010

(86) PCT No.: PCT/FR2010/050210
§ 371 (c)(1),
(2), (4) Date: Aug. 11, 2011

(87) PCT Pub. No.: WO2010/092291
PCT Pub. Date: Aug. 19, 2010

(65) Prior Publication Data
US 2011/0295288 A1    Dec. 1, 2011

(30) Foreign Application Priority Data

Feb. 10, 2009  (FR) ...................... 09 50819

(51) Int. Cl.
| A61B 17/08 | (2006.01) |
| A61B 17/11 | (2006.01) |
| A61F 2/04 | (2013.01) |
| A61F 2/00 | (2006.01) |
| A61F 2/966 | (2013.01) |
| A61F 2/95 | (2013.01) |

(52) U.S. Cl.
CPC .............. *A61B 17/1114* (2013.01); *A61F 2/04* (2013.01); *A61B 2017/1132* (2013.01); *A61F 2/0063* (2013.01); *A61F 2/966* (2013.01); *A61F 2002/041* (2013.01); *A61F 2002/045* (2013.01); *A61F 2002/9517* (2013.01)

(58) Field of Classification Search
CPC ........... A61B 17/11; A61B 2017/1135; A61B 2017/1107; A61B 17/115; A61B 17/064; A61B 2017/1117; A61B 2017/1114

USPC .................................. 606/151, 153; 623/1.15
See application file for complete search history.

(56) References Cited

U.S. PATENT DOCUMENTS

| 5,534,007 | A | * | 7/1996 | St. Germain et al. | ......... | 623/1.11 |
| 2004/0107004 | A1 | * | 6/2004 | Levine et al. | .............. | 623/23.64 |
| 2006/0064120 | A1 | * | 3/2006 | Levine et al. | ................. | 606/153 |
| 2007/0032879 | A1 | | 2/2007 | Levine et al. | | |
| 2008/0039878 | A1 | * | 2/2008 | Williams et al. | .............. | 606/153 |
| 2008/0208357 | A1 | * | 8/2008 | Melanson et al. | ......... | 623/23.65 |
| 2008/0255592 | A1 | * | 10/2008 | Hsu et al. | ...................... | 606/149 |

FOREIGN PATENT DOCUMENTS

WO    2007045229    4/2007

* cited by examiner

*Primary Examiner* — Gregory Anderson
*Assistant Examiner* — Christina Lauer
(74) *Attorney, Agent, or Firm* — Ladas & Parry LLP

(57) ABSTRACT

A surgical device (1) for temporary protection of an anastomosis (5) in the colon (12, 13, 14), the rectum (11), or the anal passage (10), including: a) a semi-rigid hollow longitudinal temporary anchor element (2), a first wall of which includes a substantially cylindrical main portion (2a) with a substantially circular section having a length (L1) of at least 50 mm, preferably in the range 70 mm to 150 mm, said first wall having an outside diameter that may be varied in a controlled manner; and b) a flexible sheath (3) fixed to said anchor element (2) against, preferably around, said first wall and having a length (L3) downstream of said anchor element (2) of at least 50 cm, preferably at least 1 m, and an outside diameter when at rest in the range 20 mm to 40 mm, preferably in the range 25 mm to 33 mm, and said sheath is made from a biocompatible elastomer material having a wall thickness in the range 0.05 mm to 1 mm.

11 Claims, 8 Drawing Sheets

SURGICAL DEVICE FOR THE TEMPORARY PROTECTION OF ANASTOMOSIS

This application is a 371 of PCT/FR2010/050210 filed on Feb. 9, 2010, which is incorporated herein by reference.

The present invention relates to a surgical device for the temporary protection of an anastomosis in the colon, rectum or anal passage.

The subject matter of the invention is thus a device for protecting an anastomosis (join) produced between the two ends of an intestinal segment to prevent or reduce the risk of separation known as anastomotic fistula. The resulting leaks may cause infections, abscesses, or peritonitis, all major causes of post-operative complications and mortality.

The technique used at present entails diverting the intestinal flow upstream of the anastomosis area. A segment of the intestine situated upstream of the anastomosis is brought out via the abdominal wall. This is known as a digestive stoma. The fecal bolus is then collected outside the abdomen, in a bag stuck to the abdominal wall around the intestine, also known as a pouch. This technique makes it possible to divert the fecal bolus upstream of the anastomosis, but at the cost of a stoma. A stoma has considerable socio-professional repercussions, however, and a significant level of local (cutaneous and intestinal) and general (dehydration) complications. Moreover, closing the stoma six to eight weeks later requires a new surgical intervention with a non-negligible mortality rate. Finally, the pouch and care of the stoma are costly.

A known alternative to a stoma is referred to as a bypass. With that technique there is no digestive diversion. The anastomosis area is protected from fecal contact by an interface. The interface is a very flexible (for example vinyl) tube that is introduced into the lumen of the intestine and attached to the proximal end thereof by a resorbable suture upstream of the area of the future anastomosis. The other end of the tube is free within the lumen of the distal intestine. The anastomosis is then produced. After an average delay of ten days necessary for proper healing of the anastomosis, and once the fixing sutures have been resorbed, the tube is spontaneously eliminated per anum with the fecal bolus.

That method was first described many years ago and the COLOSHIELD® system has been commercially available since 1992. Experimental and clinical work has confirmed the reliability of this system. However, that product has not been used by surgical teams for many years because it has several drawbacks.

One drawback of the COLOSHIELD® system is its attachment to the lumen of the intestine upstream of the future anastomosis area. That requires eversion of the proximal end of the intestine in order to expose its internal face and to fix the tube thereto by resorbable sutures. This maneuver is the source of traction on, injury to, or tearing of the intestine at the very place where it must be joined to the distal end of the intestine. Another drawback of that system is the impossibility of using an automatic circular stapler to produce the anastomosis. More than 80% of colorectal anastomoses are produced using such machines.

WO 03/094785 discloses a conical or funnel-shaped permanent anchor element made from a plastics material provided with a valve implanted permanently at the start of the digestive tube, notably in the small intestine, and coupled to a flexible sheath extending into the small intestine downstream of said anchor element, that system being intended to treat obesity. Said anchor element has an outside diameter slightly greater than that of the intestine, even in its dilated phase during intestinal transit, because said anchor element must remain fixed to the stomach permanently by sutures.

US 2008/0208357 discloses a method of the curative treatment of fistulas, i.e. leaking of the contents of the intestine at a gastro-intestinal anastomosis, the method including the use of an anchor element consisting of a stent 25 millimeters (mm) to 45 mm long and 20 mm to 40 mm in diameter coupled to a short flexible sheath for repairing and blocking the fistula or leak. That stent is introduced into the esophagus via the mouth and installed above the area of reduced anatomical section at the junction between the esophagus and the stomach. The stent installed in the oesophageous in this manner must not migrate and in any event is prevented from migrating by virtue of its installation upstream of the area of reduced anatomical section at the junction between the esophagus and the stomach.

In US 2008/0208357 the length of the sheath is necessarily less than the length of the jejunal loop that is anastomosed to the stomach (approximately 60 centimeters (cm)). The device must necessarily be introduced via the mouth, as mentioned above. Once the stent is in place, the sheath must be pushed downstream of the stent so as to be deployed in the jejunal loop. The total distance between the oral cavity and the distal end of the deployed sheath is in the range 57 cm to 72 cm. In practice, it would not be possible to deploy a sheath longer than 15 cm to 30 cm by pushing it in this way. Moreover, that maneuver of pushing in the sheath is hazardous for the anastomosis because it is effected in an area that is greatly weakened by the fistula and may aggravate the state of the fistula.

Finally, in US 2008/0208357 the sheath is very thin (in the range 0.01 mm to 0.025 mm thick), because in this application the sheath must not irritate the esophagus, which is particularly sensitive. However, because it is so thin, that kind of sheath cannot have shape memory. It may be subject to plication or twisting. That is why the above patent refers to another patent, U.S. Pat. No. 7,267,794, relating to the use of a device in the form of a circular metal wire that prevents twisting of the sheath.

The problem addressed by the present invention is to provide a device for temporary protection of an anastomosis of the bypass type in the colon, which device is inserted after producing the anastomosis and regardless of the technique used (suture or stapler), it requires no fixing maneuvers, and it is eliminated spontaneously without surgical intervention after a sufficient delay following healing of the anastomosis.

To this end, the present invention provides a surgical device for temporary protection of an anastomosis in the colon, rectum, or anal passage, the device including:

a) a semi-rigid hollow longitudinal element called temporary anchor element, a first wall of which defines a surface of revolution about a longitudinal axis XX, including a substantially cylindrical main portion with a substantially circular section, and said first wall having an outside diameter that may be varied in a controlled manner between:

a reduced outside diameter D1' of at most 10 mm in a radially retracted configuration of said first wall; and a maximum outside diameter D1 in a maximum radial expansion configuration of the main portion of said first wall in the range 20 mm to 40 mm, preferably in the range 25 mm to 33 mm; and b) a sheath having a flexible tubular wall fixed against, preferably around, said first wall of said anchor element (2); which device is characterized in that:

1) said first wall of said temporary anchor element includes a said main portion of greater diameter having a length L1 of at least 50 mm, preferably in the range 70 mm to 150 mm; and 2) said sheath has when at rest a length L3 downstream of said anchor element of at least 50 cm, preferably at least 1 meter (m), and an outside diameter in the range 20 mm to 40 mm, preferably in the range 25 mm to 33 mm, and is made from a biocompatible elastomer material having a wall thickness in the range 0.05 mm to 1 mm.

The reduced outside diameter $D'_1$ in the radially retracted configuration of said first wall makes it possible to introduce said anchor element in this radially retracted configuration per anum and then to route it in the colon as far as a temporary anchor position upstream of an anastomosis in the colon, rectum, or anal passage, and the maximum outside diameter $D_1$ in the maximum radially expanded configuration of said wall makes it possible for said anchor element, in the absence of intestinal transit, to remain temporarily anchored by the radial expansion force against the intestinal wall and to be released and begin to migrate when the intestine contracts and expands during what is called the peristaltism phase on resumption of intestinal transit.

With reference to said anchor element:
the expression "semi-rigid" means that in each of the retracted and expanded configurations said first wall of said anchor element retains a given shape defining a said surface of revolution; and
the expression "outside diameter that may be varied in a controlled manner" means that the diameter of said first wall may vary in a manner determined as a function of conditions of use of the device, regardless of parameters such as temperature, and/or independent mechanical means cooperating with said anchor elements such as a fitting instrument, notably an introducer sheath, as explained below.

It is clear that said anchor element may adopt:
a reduced outside diameter $D'_1$ of said first wall at least less than that of the intestine when at rest, preferably less than 10 mm, so that it may be introduced per anum as far as the upstream side of an anastomosis in the intestine; and
an outside diameter $D_1$ in the maximum radially expanded configuration of said first wall greater than or equal to that of the intestine when at rest so that it may be temporarily anchored by virtue of bearing on the intestinal wall by radial expansion at least over a part of said anchor element, the diameter $D_1$ always remaining less than the maximum diameter of the intestine in the peristaltism phase so that said anchor element remains fixed against the wall of the intestine in the absence of intestinal transit, notably during the post-operative paralytic ileus phase of intestinal paralysis, but is no longer fixed to the intestine and in practice upon resumption of intestinal transit begins to migrate by sliding along the intestinal wall.

A standard way to determine the diameter $D_1$ is to calibrate the section of one of the ends of the intestine by means of instruments known as bougies, which are routinely used by surgeons. Another way to determine the diameter $D_1$ is, where applicable, to consider it equal to the diameter of the stapler used to produce the mechanical anastomosis. The diameter $D_1$ may then more particularly vary in the range 25 mm to 33 mm, corresponding to the outside diameter of staplers commercially available at present.

The expression "longitudinal end" means an end of said anchor element or where applicable said sheath in the longitudinal direction.

References to the length and diameter of the sheath "when at rest" mean its length and diameter respectively when its longitudinal and radial elasticity are not loaded.

After resumption of intestinal transit, peristalsis of the intestine results in release of said anchor element and migration of the released anchor element, but the radial expansion properties of the anchor element enable its external wall to continue to slide in contact with the internal wall of the intestine and thus to produce a sufficient seal and therefore to continue to protect the anastomosis by preventing the fecal bolus passing between the outside wall of the anchor element and the inside wall of the intestine. The fecal bolus must travel through the sheath and remains well separated from the intestinal wall at the level of the anastomosis.

The above values of the radially expanded diameter of the anchor element are slightly greater than the diameter of the intestine when at rest, varying according to the patient but less than the maximum diameter of the intestine when dilated during intestinal transit, which is in the range 30 mm to 60 mm. Moreover, the length of said main portion is such that the area of contact between said anchor element and the wall of the colon combined with the radial expansion force are such that said anchor element in the maximum expansion configuration remains temporarily fixed by virtue of its radial expansion force against the wall of the intestine upstream of the anastomosis and does not migrate in the absence of intestinal transit for at least three days, preferably five days, after it is anchored. Without a length of at least 50 mm of the main portion in contact with the colon, said anchor element could not remain anchored for at least three days without using fixing means, thereafter requiring means and/or interventions to deactivate the fixing means and enable its migration, or without using anchor elements having a larger maximum expansion diameter, which could injure the colon and besides could prevent natural release of the anchor element on resumption of transit.

In contrast, the length of the sheath is such that the distance between the anastomosis and the upstream anchor site may be at least 50 cm, preferably at least 1 m, and said anchor element may be anchored in the colon sufficiently upstream of the anastomosis for its migration time between said anchor position and said anastomosis on resumption of transit to be at least three days, preferably at least six days, and for said sheath to protect the anastomosis, or even to project per anum when said anchor element is in the anchor position.

Accordingly, given that the post-operative intestinal paralysis phase known as paralytic ileus lasts three to five days, it is possible to protect the anastomosis in this way for the same period plus the time that said anchor element takes once released to migrate between its anchor site upstream of the anastomosis and the site of the anastomosis, this migration time depending on the distance to be travelled between the anchor site and the anastomosis. In practice, a distance of 50 cm to 1 m is reflected in a migration time of three to six days, so that in total the anastomosis is protected for at least six to eleven days after it is produced.

Clearly, because it consists of an elastomer, said sheath has radial and longitudinal stretch properties similar to those of the intestinal wall, which properties are those of an elastomer material (the sheath) having radial and longitudinal elasticity properties. These radial and longitudinal elasticity properties of the sheath are similar to those of the wall of the colon and enable intestinal transit to be effected correctly in said sheath throughout the period of migration of the anchor element, that is to say at least six to ten days.

The longitudinal elasticity of the elastomer sheath may be greater than that of the intestine without causing problems, and to the contrary has the advantage that the sheath portion projecting per anum may be pulled on, in order to cut it, and then retract in the upstream direction, inside the rectum.

By virtue of its radial elasticity, said longitudinal end of the sheath remains fixed to said end of said anchor element whatever its radial expansion.

Moreover, the thickness characteristics of the sheath combined with its elasticity give it shape memory properties. Here the expression "shape memory properties" refers to the fact that the elastomer material of said sheath naturally returns to its initial shape after it is deformed by bending. Given the great length of the sheath, the shape memory properties are important for the material to resume its longitudinal shape naturally without blocking transit in the event of plication of the sheath, which may occur during its migration after releasing the anchor element.

In a preferred embodiment said main portion of said first wall extends from the upstream longitudinal end of said first wall as far as an appropriately shaped downstream end portion having a smaller diameter than the cylindrical main portion, the outside diameter D2 of the downstream end of said first wall in the maximum radial expansion configuration being in the range 20 mm to 35 mm and the length L2 of said appropriately shaped end portion of the first wall being in the range 10 mm to 30 mm, preferably in the range 15 mm to 25 mm, the diameter of said end portion preferably decreasing progressively between said main portion and said downstream end of said first wall.

To prevent jamming at this level, the appropriately shaped downstream portion of the anchor element facilitates its migration through the anastomosis area, which generally has a reduced passage diameter compared to the colon upstream and downstream of the anastomosis area. This reduced diameter is the result of a stenosis at the level of the anastomosis. In contrast, an appropriately shaped upstream portion of the anchor element would lead to the risk of leakage between the anchor element and the intestinal wall.

More particularly, the diameter of said appropriately shaped downstream end portion is reduced by surrounding it with an elastomer material ring having a diameter less than said diameter of said main portion in said maximum radial expansion configuration.

Preferably:
said anchor element is made from a material conferring on it radial elasticity properties such that it may be compressed radially in said retracted configuration and adopt said maximum radial expansion configuration after the radial compression is released; and
said sheath is made from an elastomer-based biocompatible polymer material of the silicone or polyurethane type having a wall thickness in the range 0.1 mm to 0.5 mm and having radial and longitudinal elasticity properties, shape memory properties, and non-stick properties.

The expression "non-stick properties" refers to the fact that the elastomer material of said sheath has a coefficient of adhesion such that the two opposite surfaces of the inside wall of the sheath do not stick together on folding and therefore do not create any resistance to the passage of gas and material.

Said anchor element may be held in the radially retracted configuration with an instrument known as an introducer sheath described below, radial expansion occurring after disengagement of the anchor element from the introducer sheath.

It is also clear that:
said sheath has a diameter when at rest substantially as least equal to said reduced outside diameter $D'_1$ of said hollow anchor element when radially retracted and less than that of the intestine when at rest, and said diameter of said sheath when at rest is preferably substantially equal to that of the intestinal wall when at rest; and
said sheath extends downstream of the end of said anchor element to which it is fixed over a length corresponding to the distance between the anchor position upstream of said anastomosis and a downstream position, preferably as far as the anal orifice.

More particularly, the thickness of said first wall of the anchor element is in the range 0.5 mm to 5 mm, preferably in the range 1 mm to 3 mm.

The longitudinal elasticity of the elastomer sheath may be greater than that of the intestine without causing any problems, and to the contrary has the advantage that if necessary it is possible to pull on the portion of the sheath protruding from the anus, so as to be able to cut it, and that it then retracts inside the rectum or the anal passage.

Said first wall of said anchor element may be solid or perforated, notably by pores or miniperforations.

In one particular embodiment, said hollow longitudinal temporary anchor element is a stent-type enteral prosthesis the tubular wall of which is covered on at least its outside surface with a biocompatible synthetic material coating, preferably a silicone or polyurethane type elastomer.

This external coating is doubly advantageous in that it facilitates deployment of said anchor element by sliding it along the intestinal wall on resumption of transit and in that during anchorage it protects the intestinal wall against which said longitudinal element is expanded; this element could otherwise become incorporated into the tissue of the intestinal wall and prevent subsequent re-release, or even perforate the intestinal wall.

These stent type enteral prostheses have been used on intestinal tumors for some twenty years, mainly in the palliative treatment of tumoral stenosis (shrinkage) of the esophagus, duodenum, or colon. They were not designed for temporarily anchoring a device for protecting an intestinal anastomosis in the manner of the present invention. In other words, there has never been proposed an enteral prosthesis attached to a flexible sleeve, the assembly being designed with the dimensional characteristics and notably the elasticity characteristics defined above to protect a digestive anastomosis.

The temporary anchor element is preferably an enteral prosthesis the first wall of which is formed by a spiral mesh of metal or elastomer material filaments, notably filaments of an elastomer material based on silicone, preferably coated with a layer of biocompatible synthetic material that covers said mesh, said coating preferably being a biocompatible elastomer material such as silicone.

As is known in the art, radial expansion is then the result of the metal wires crossing at an angle that varies, thus varying the width of the lozenge or parallelogram shape of the meshes of said spiral wire mesh.

The anchor element is advantageously made from a material that confers on it expansion by radial elasticity properties only at a temperature at least equal to an ambient temperature of 20° C., notably at the temperature of the human body, said anchor element being in said radially retracted configuration at a temperature below said ambient temperature, preferably below 5° C. Clearly the tubular material changes diameter automatically as a function of ambient temperature.

Even more particularly, said anchor element is an enteral prosthesis said first wall of which is formed by a spiral wire, preferably nitinol wire, mesh.

Nitinol is a metal alloy having properties of progressive radial expansion as a function of temperature at a temperature greater than or equal to ambient temperature (25° C.), enabling it to retain its retracted shape at lower temperatures, notably in storage at 4° C. Once retracted at low temperature, it remains retracted in this way for long enough to be able to place it in the introducer sheath and to route it in the intestine using said introducer sheath. Once released inside the intestine, the prosthesis progressively expands in the radial direction because of the effect of a higher ambient temperature, namely that of the human body.

In one particular embodiment, the connection between said sheath and the anchor element is such that the end of said sheath adheres to and elastically covers at least the surface of the longitudinal end of said hollow longitudinal element.

In a preferred variant, said sheath adheres to and elastically covers the outside surface of said anchor element at least over the outside surface of the downstream end of said anchor element. Said sheath thus has a coating function and where applicable covers the mesh of the anchor element.

The above two embodiments may use for the fabrication of the sheath a method of dipping a solid molding tube, where appropriate in line with an anchor element, into a bath of said polymer composition, onto which tube said polymer material is molded, said hollow longitudinal element being threaded onto said solid molding tube before dipping.

To provide the radial expansion properties of the elastomer sheath, given the thickness employed (in the range 0.05 mm to 0.4 mm), it is necessary to use elastomer compositions having some hardness, as well as stickability (adhesion coefficient), and shape memory (DRC, degree of remanent compression), the selected value ranges of which are explained below.

More particularly, said sheath is made from an elastomer-based biocompatible polymer material, preferably of the silicone and/or polyurethane type, having the following properties:
  a Shore A hardness in the range 5 to 95, preferably in the range 50 to 70;
  a degree of remanent deformation on compression (RDC) in the range 10% to 35%, preferably in the range 17% to 23%; and
  a coefficient of friction in the range 0.30 to 0.90, preferably in the range 0.35 to 0.45.

The term "hardness" refers to the energy of elastic deformation of an elastomer, here expressed as a Shore A hardness, for example, in accordance with the DIN 53505 standard.

The expression "degree of remanent compression" (DRC) refers to the degree of residual deformation after releasing a load on an elastomer sample after a particular time, according to the test specified in the DIN 53517 ISO 815B standard, for example the shape memory property on bending, the material reverting to an unbent shape as soon as the compression that caused it to bend is released.

The coefficient of friction may be measured according to the ASTM D1894 standard, for example.

The above values of the coefficient of friction prevent adhesion between two opposite faces of the internal wall of the sheath when in contact each other, firstly so as not to create any resistance to the passage of gases and materials in the sheath and secondly so that if it is bent, the sheath is not blocked by closing on itself.

Even more particularly, said sheath is made from a biocompatible polymer material based on silicone including at least the following compounds:
  75 wt % to 95 wt % of a liquid silicone rubber (LSR) grade or quality elastomer;
  2.5 wt % to 12.5 wt % of an RTV grade or quality elastomer; and
  2.5 wt % to 12.5 wt % of a gel grade or quality elastomer.

This combination of elastomers of different grades (LSR, RTV, gel) is advantageous because:
  an LSR grade or quality elastomer contributes resistance to tearing;
  an RTV grade or quality elastomer contributes radial and longitudinal elasticity properties; and
  a gel grade or quality elastomer contributes a reduced coefficient of adhesion (non-stick property).

In a preferred embodiment, said anchor element is a stent-type enteral prosthesis covered on at least its outside surface with a coating of silicone or polyurethane type elastomer synthetic material, said elastomer coating being more flexible than the elastomer material of said sheath, the connection between said sheath and said anchor element being effected by said sheath covering said anchor element over only part of the length of said anchor element including at least its appropriately shaped downstream end of progressively reducing diameter.

Stent-type enteral prostheses of this type coated with elastomer, notably a silicone-based elastomer, are well known in the art and commercially available. Thus the elastomer coating of the stent has greater radial and longitudinal deformability than the elastomer of the sheath, i.e. the elastomer coating of the stent consists where appropriate of a mixture of different types of RTV grade silicone having a weight percentage greater than that of the elastomer of the sheath but still within the 2.5 wt % to 12.5 wt % range referred to above.

As explained below, by applying traction to the sheath, this embodiment makes it possible to induce a diameter reduction and axial elongation of the stent enabling it to be detached from the intestine to facilitate its migration through the anastomosis on release of said anchor element.

A stent type anchor element is advantageously used that includes at its ends an elongate or thread-like extension known in the art as a lasso, making it possible, in a manner known to the person skilled in the art, and where applicable using a tool such as a colonoscope, to apply traction to the end of said stent type anchor element in order to facilitate its release and/or its migration via the anastomosis area when this is required, in order to prevent it jamming at this level.

Said polymer material of said sheath advantageously includes radio-opaque, notably barium sulfate, filaments disposed in the longitudinal direction of the tube.

These filaments make it possible to track the migration of the sheath and to monitor its initial positioning and thereafter its progressive migration during its elimination. Moreover, the longitudinal disposition of these filaments confers simultaneously on the sheath resistance to elongation and reduced longitudinal elasticity, which otherwise might be excessive, for example compared to that of the intestine (see above).

The sheath is advantageously graduated in the increasing direction starting from its upstream end.

More particularly, the introducer sheath may in known manner consist of a semi-rigid guide tube of the catheter type provided at one of its ends with a handle and the inside diameter and the length of which enable accommodation therein of said anchor element in its retracted form and said sheath, preferably deployed longitudinally.

Nevertheless, said device preferably further includes an introducer sheath including:
  a tubular external envelope that is adapted to contain said anchor element when compressed in said retracted configuration and to retain it inside the distal end of said external envelope and is sufficiently long also to contain said sheath, said external envelope preferably having a length of at least 110 cm, preferably at least 150 cm; and
  means for routing the distal end of said introducer sheath from the anal orifice to said anchor site in the intestine upstream of the anastomosis; and
  preferably, means for disengaging said anchor element from the external envelope, preferably in the form of a buffer tube including an abutment at its distal end, where appropriate in contact with the longitudinal end of said anchor element, said sheath downstream of the anchor element surrounding said buffer tube inside said external envelope.

The shrinkage of the external envelope and then of the buffer tube enable complete deployment of the sheath downstream of the anchor element without any additional maneuver by the surgeon being necessary to deploy the sheath.

The device of the invention preferably further includes a protector tube, preferably a protector tube having an outside diameter in the range 20 mm to 40 mm and a length in the range 10 mm to 25 cm, that includes a portion of curved shape conforming to the curvature of the sacral concavity, is stiffer than the external envelope of the introducer sheath, has an outside diameter and length such that said protector tube may be introduced via the anal orifice and extend between the anal orifice and a point upstream of said anastomosis, and has an inside diameter and a curvature conforming to the curvature of the sacral concavity such that said protector tube is able to contain said introducer sheath and route it between the anal orifice and said anastomosis.

The present invention enables the use of a surgical treatment method employing a surgical device of the invention to provide temporary protection of an anastomosis in the large intestine or colon, the rectum, or the anal passage, in order to prevent or reduce the risk of anastomotic fistula, by effecting the following successive steps:

1) Said surgical device is introduced per anum and routed as far as an anchor site upstream of the anastomosis area, the anchor element being retained in said radially retracted configuration with diameter $D'_1$ and routed using an instrument known as an introducer sheath and the length of said elastomer sheath being at least equal to the distance between the anchor site and the anal orifice.

2) The introducer sheath is disengaged from said anchor element once it has been routed to said anchor site to enable said anchor element to adopt an anchor position against the intestinal wall in said maximum radially expanded configuration.

The distance between said anchor position and said anastomosis is preferably at least equal to the distance travelled by said anchor element in at least three days, preferably at least five days, when migrating once released from said intestinal wall and by the resumption of intestinal transit.

More particularly, the distance between the anastomosis and the anchor site is at least 50 cm, preferably at least 1 m.

Even more particularly, in the absence of resumption of intestinal transit said anchor element remains anchored in said anchor position for at least three days, preferably at least five days, after it is anchored.

Accordingly, given that the post-operative intestinal paralysis phase known as paralytic ileus lasts from three to five days, it is possible in this way to protect the anastomosis for the same period, plus the time that said anchor element takes to migrate after it is released between its anchor site upstream of the anastomosis and the site of the anastomosis, given that this migration time depends on the distance to be travelled between the anchor site and the anastomosis. In practice a distance of 50 cm to 1 m is reflected in a migration time of three to six days, so that in total the anastomosis is protected for six to eleven days after it is produced.

Said introducer sheath is preferably introduced by pushing it inside a semi-rigid protector tube, the protector tube preferably having outside diameter in the range 20 mm to 40 mm and a length in the range 10 mm to 25 cm, which includes a part of curved shape conforming to the curvature of the sacral concavity, is of greater stiffness than the external envelope of the introducer sheath, has outside diameter and length such that said protector tube can be introduced via the anal orifice and extend between the anal orifice and as far as a point upstream of said anastomosis, and has an inside diameter and a curvature, conforming to the curvature of the sacral concavity, such that the protector tube is able to contain said introducer sheath and to enable it to be routed between the anal orifice and said anastomosis, the latter tube extending between the anal orifice and said anastomosis.

Once released from said intestinal wall, the migrating anchor element is preferably recovered by a resumption of intestinal transit in a protector tube, preferably taking the form of a tube having an outside diameter in the range 20 mm to 40 mm and a length in the range 10 cm to 25 cm, that has a semi-rigid curved part conforming to the curvature of the sacral concavity, is of greater stiffness than the external envelope of the introducer sheath, has an outside diameter and length such that said protector tube may be introduced via the anal orifice and extend between the anal orifice and a point upstream of said anastomosis, and has an inside diameter and a curvature, conforming to the curvature of the sacral concavity, such that the protector tube is able to contain said introducer sheath and to enable it to be routed between the anal orifice and said anastomosis, the protector tube extending between the anal orifice and said anastomosis.

Other features and advantages of the present invention become apparent in the light of the following detailed description given with reference to FIGS. 1 to 11, in which.

Figure 4:
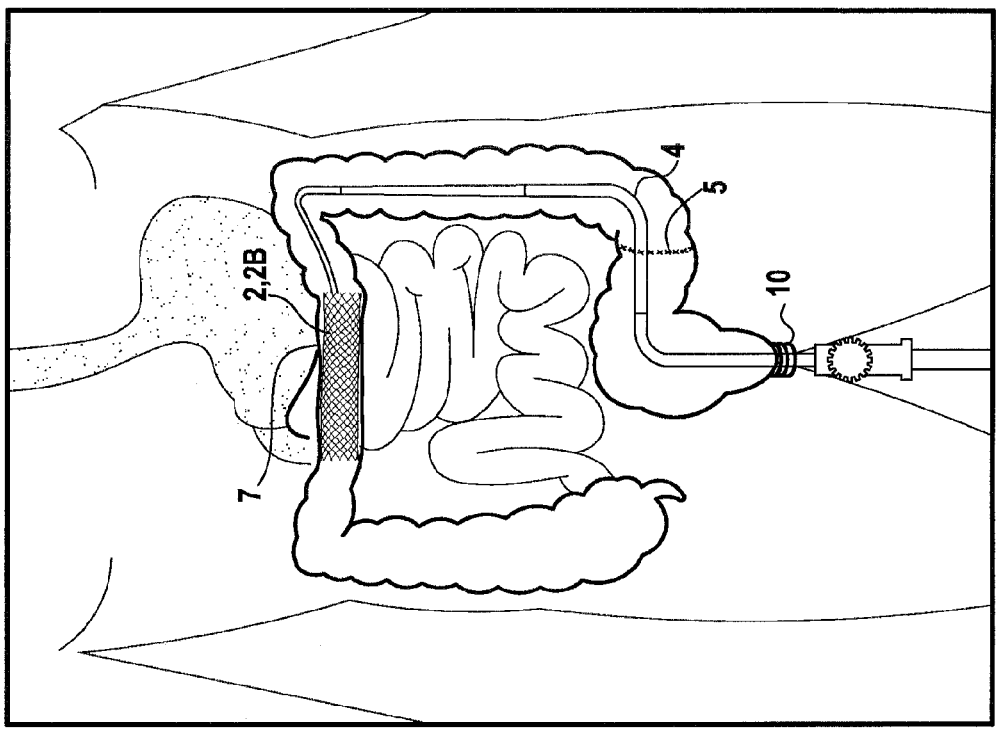
Figure 5:
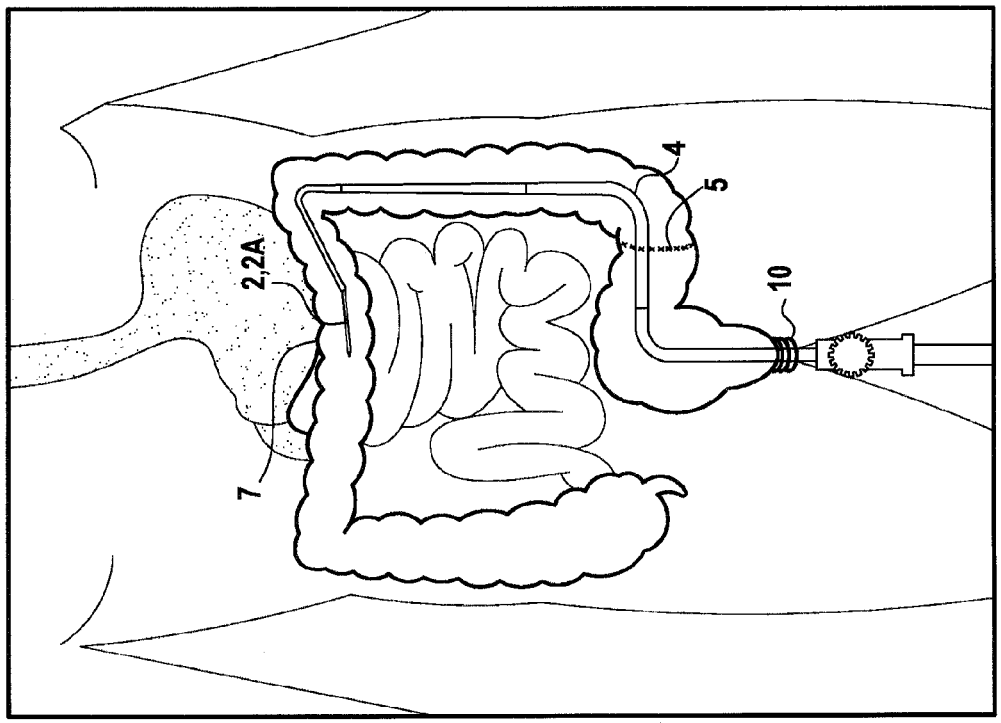
Figure 6:
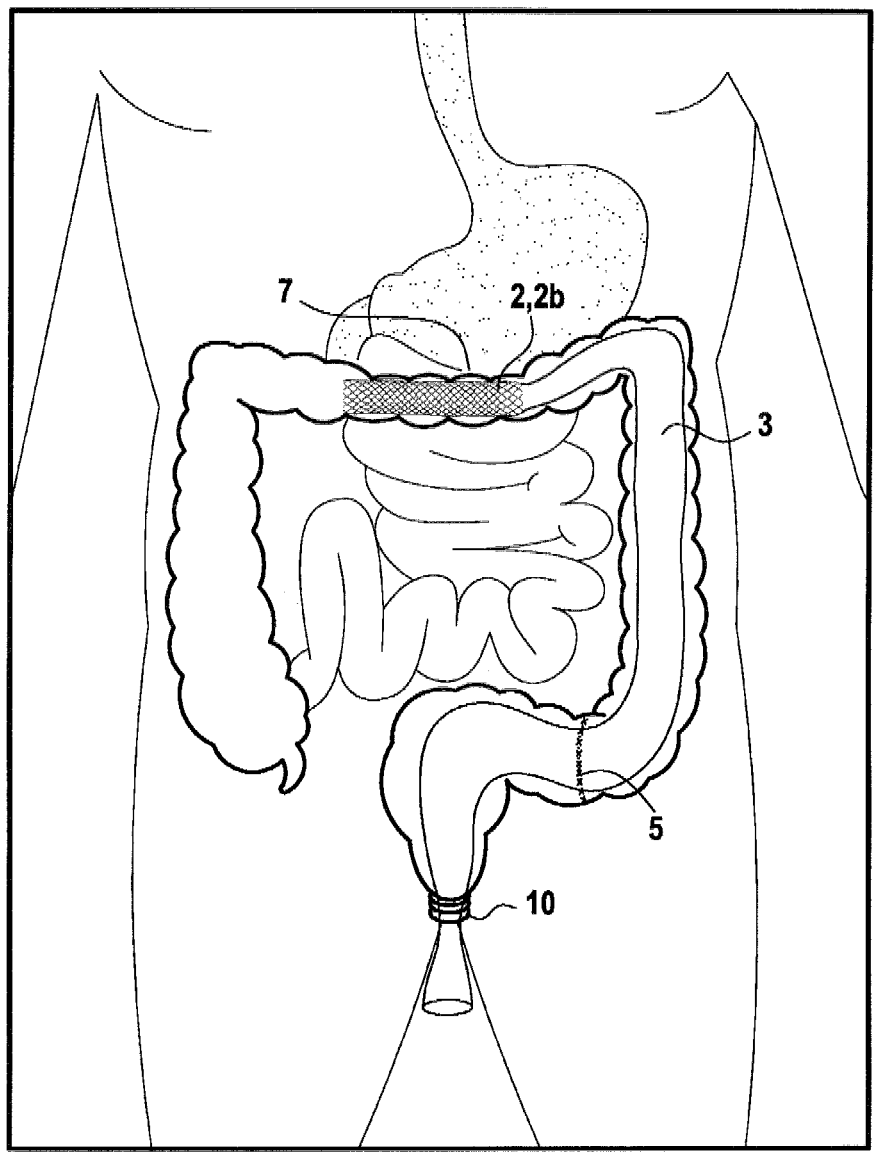
Figure 7B:
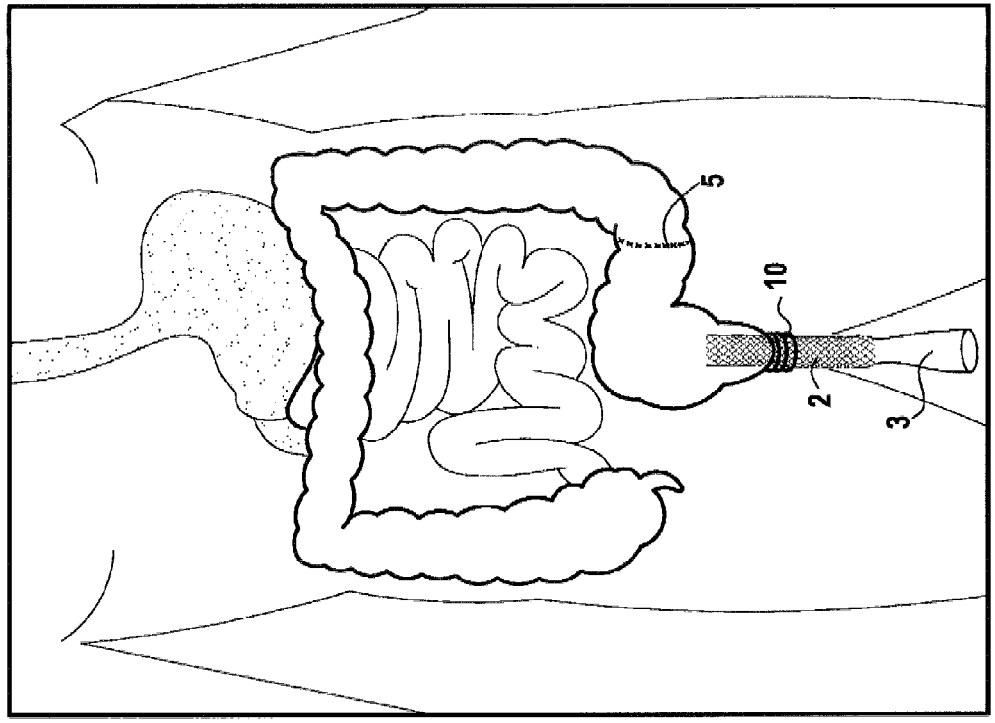
Figure 7A:
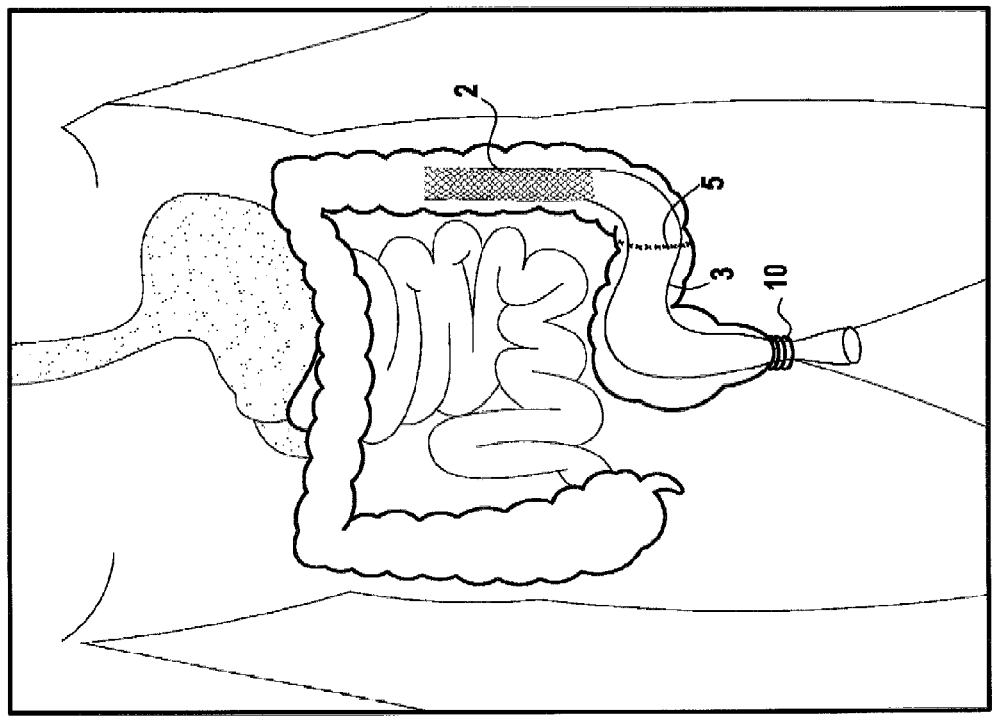
Figure 8:
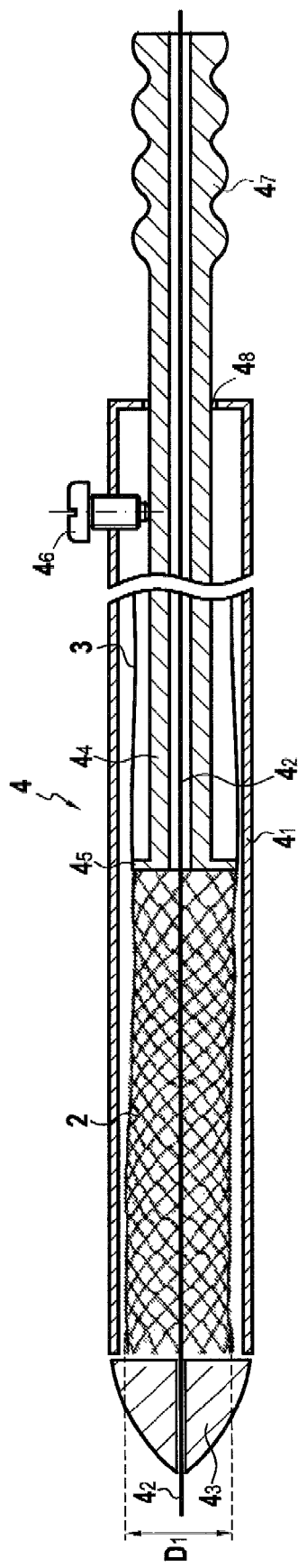
Figure 9:
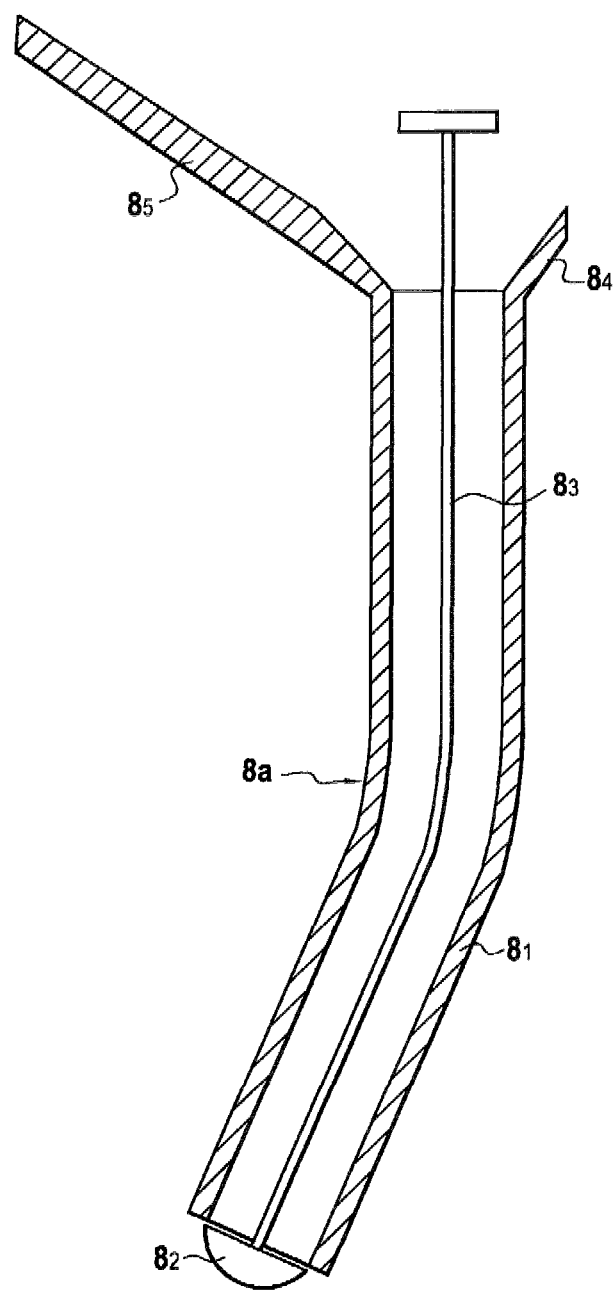
Figure 10:
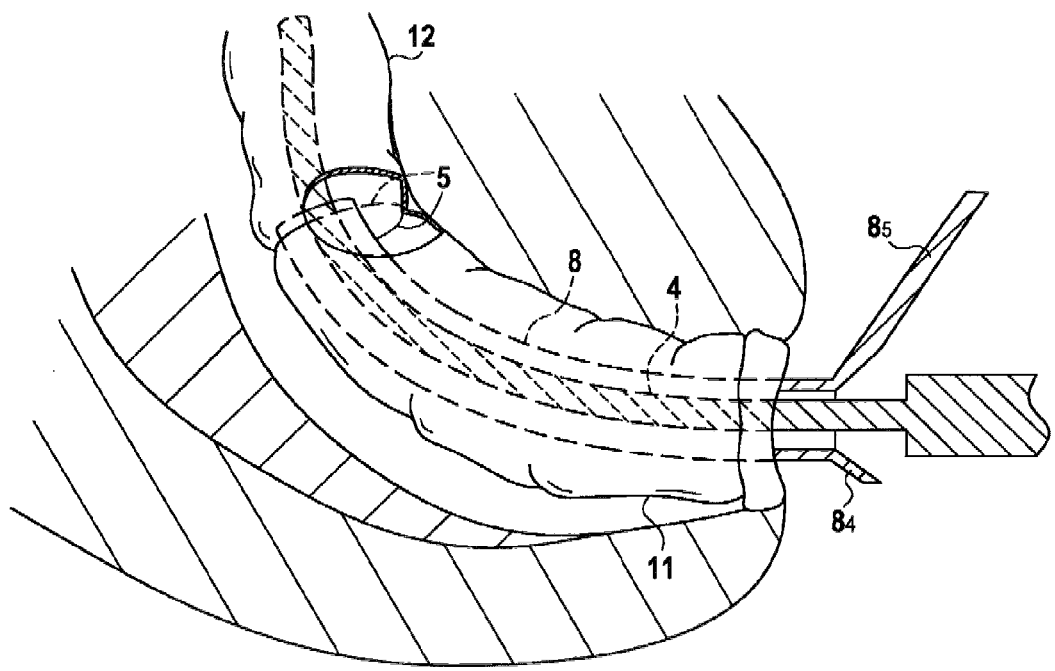
Figure 11:
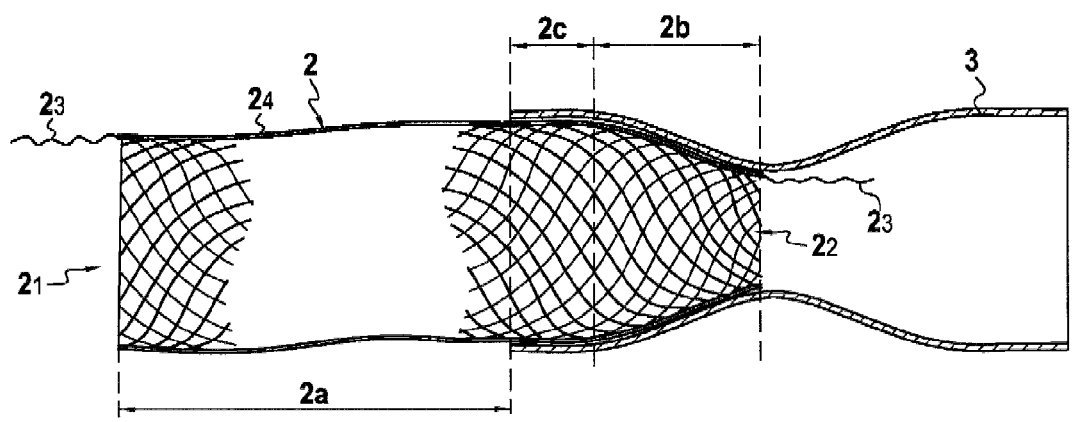

FIG. 4 is a diagrammatic view of the device of the invention routed to its implantation site via an introducer sheath 4, the anchor element 2 being in its retracted radial configuration on leaving the introducer sheath and the sheath 3 still being housed inside the introducer sheath;

FIG. 5 represents part of the device of the invention in the anchor position, the anchor element being retained in the maximum radially expanded configuration and immobilized against the intestinal wall;

FIG. 6 represents diagrammatically the device of the present invention in an anchor position in which the anastomosis is protected, the sheath 3 being deployed downstream of the anchor element 2;

FIGS. 7A and 7B represent the device of the invention when migrating during the elimination peristalsis phase (FIG. 7A) and at the end of elimination (FIG. 7B);

FIG. 8 represents an introducer sheath of the invention;

FIG. 9 represents a protector tube of the invention;

FIG. 10 represents an introducer sheath of the invention passed through the protector tube at the level of the sacral concavity; and FIG. 11 is a diagrammatic view of a device of a preferred embodiment of the invention.

Figure 1:
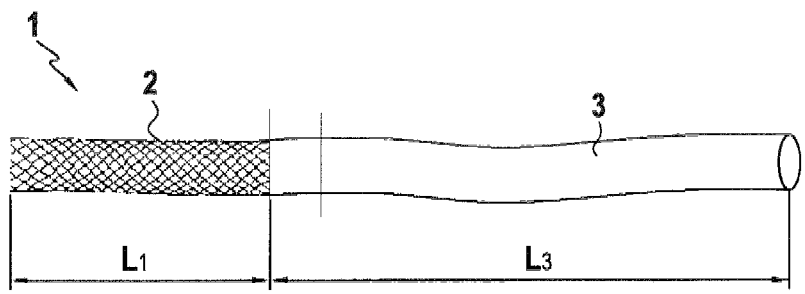
FIG. 1 represents diagrammatically a device of the invention.

FIG. 1 shows a surgical device of the invention including:
an anchor element 2 consisting of an enteral prosthesis of the type described below in a maximum radially expanded configuration; and a flexible silicone sheath 3 attached to the downstream end of the cylindrical enteral prosthesis and extending over a length L3 at least twice the length of the anchor element 2.

The prosthesis 2 is a known device called a stent made in particular from nitinol, the physical properties of which are known to the person skilled in the art. Stents are small tubes having controlled radial expansion properties as a function of temperature. To be more precise, they undergo progressive radial expansion if their temperature rises above approximately 20° C. This element is produced in the form of a spiral nitinol wire mesh entirely coated with one or more layers of silicone.

Figure 2:
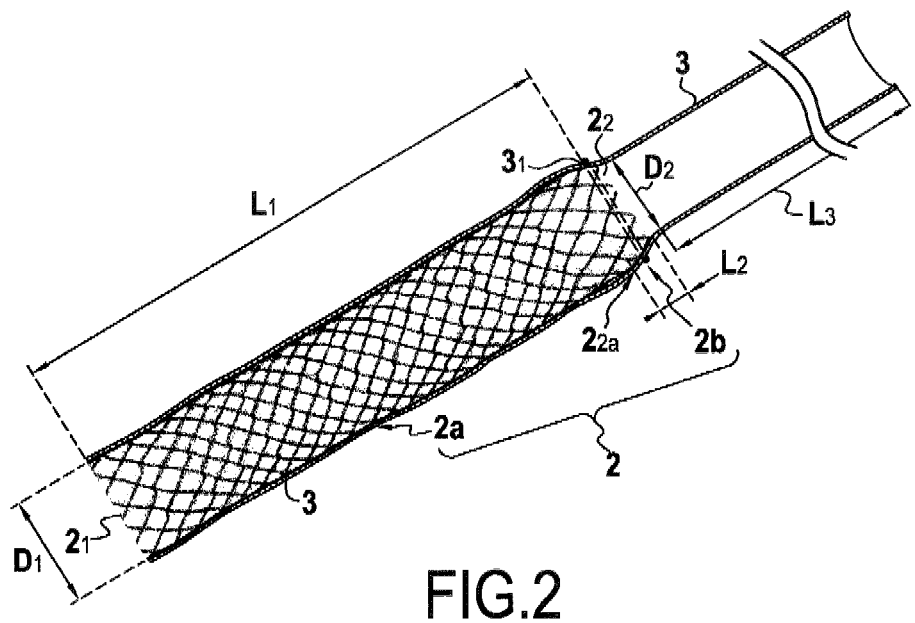
FIG. 2 is a view in longitudinal section of a device of one embodiment of the invention with a downstream end portion 2b of an appropriately shaped anchor element having a reduced diameter compared to a cylindrical main portion.

FIG. 2 represents a preferred variant of the anchor element or stent 2 in which said main portion 2a of said first wall extends from the upstream longitudinal end $2_1$ of said first wall as far as an appropriately shaped downstream end portion 2b of smaller diameter than the cylindrical main portion. The diameter D1 of the cylindrical main portion at its maximum radial expansion is approximately 32 mm. The outside diameter D2 of the downstream end $2_2$ of the first wall at its maximum radial expansion is approximately 24 mm. The length L1 of the cylindrical main portion is approximately 70 mm. The length L2 of the appropriately shaped end portion 2b of the first wall is approximately 20 mm. The diameter of said end portion 2b decreases progressively between the downstream end $2_2$ of said main portion 2a and said downstream end $2_2$ of said first wall.

To be more precise, the diameter of the appropriately shaped downstream end portion 2b is reduced by surrounding it with an elastomer material ring $3_1$ that has a diameter less than said diameter of said main portion at its maximum radial expansion.

In the retracted configuration, this prosthesis 2 may adopt a diameter in the range 3 mm to 8 mm.

The sheath 3 and the elastic ring $3_1$ are made from a biocompatible elastomer material based on silicone or polyurethane.

In an embodiment represented in FIG. 2, the upstream end of the sheath covers the anchor element 2 over the whole of its length, which latter element is embedded in the elastomer constituting the sheath, which makes it possible to coat all the external surface of said anchor element 2 as well as providing the connection between the sheath and the anchor element 2.

Said sheath when at rest has a length downstream of said anchor element of at least 50 cm, preferably at least 1 m, a diameter $D_2$ in the range 26 mm to 33 mm, and a wall thickness in the range 0.1 mm to 0.5 mm.

This distance of at least 50 cm, preferably 1 m, makes it possible to envisage an implantation site 7 for the anchor element 2 at a distance upstream of the anastomosis 5 of at least 50 cm, or at least approximately 1 m, as the case may be.

The sheath 3 is produced from a mixture of different types of silicone (LSR, RTV, and gel), as described above.

The surgeon produces the anastomosis by the usual method, often employing a stapler. Once the anastomosis has been produced, the assistant inserts the introducer sheath.

Figure 3:
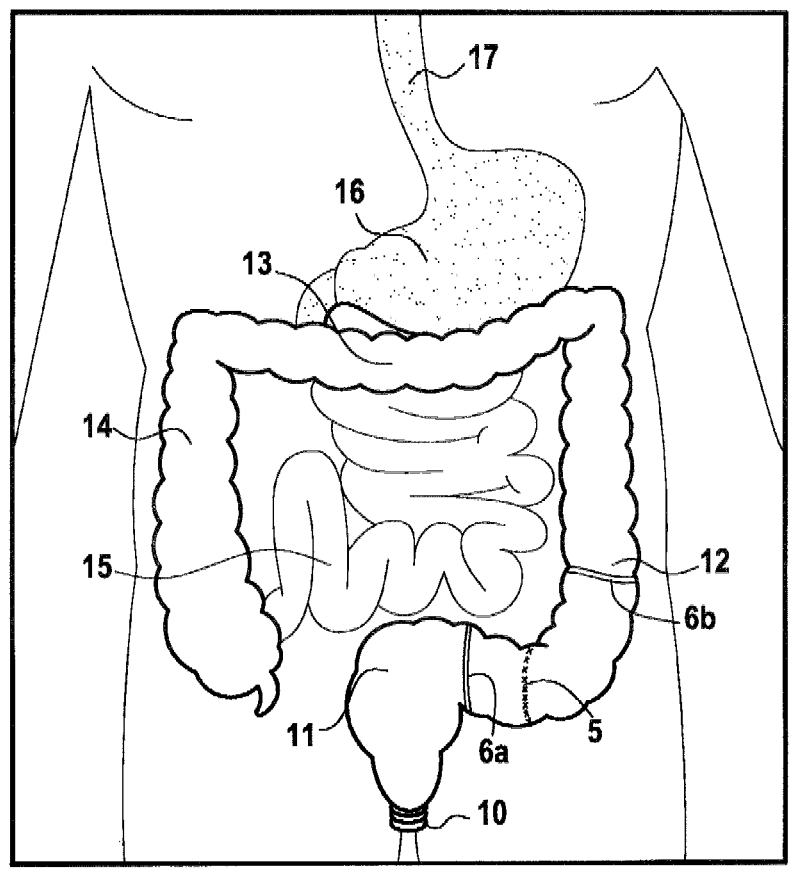
FIG. 3 is a diagrammatic view of the digestive system, with an anastomosis 5.

FIG. 3 represents the various portions of the intestine, namely the rectum 11, the anal passage 10, the descending colon 12, the transverse colon 13, the ascending colon 14, the small intestine 15, the stomach 16, and the esophagus 17.

There are represented the two ends 6a and 6b of the resected intestine segment and the join 5 between these two ends constituting the anastomosis.

FIG. 4 shows the insertion of the device of the invention, which is inserted in a retracted configuration 2A via an introducer sheath 4 that consists of a deformable semi-rigid plastics material tube with a diameter in the range 3 mm to 8 mm and a length in the range 70 cm to 220 cm, into which the anchor element is inserted in retracted form, said sheath being positioned downstream of the anchor element inside the guide tube of the introducer sheath. Once the guide tube of the introducer sheath has reached the implantation site 7, for example a point approximately 1 m upstream of the anastomosis 5, the anchor element may exit the end of the introducer sheath and adopt an expanded configuration 2B shown in FIG. 5. It should be noted that the time taken to introduce the introducer sheath of the anchor element and to route it to the implantation site 7 is in practice less than the time after which said anchor element expands radially because of the increase in temperature to which it is exposed inside the body.

FIG. 6 represents the complete device with the sheath 3 deployed after withdrawing the introducer sheath 4. The sheath 3 extends from the implantation site 7 as far as the anal orifice 10.

Initially closed and housed inside the introducer sheath, the stent has a very small diameter, notably in the range 3 mm to 8 mm. It passes through the anastomosis 5 and then enters the upstream intestine 12. The surgeon assesses the progress of the introducer sheath 4 and its correct placement by palpating the introducer sheath via the intestinal wall and visualizing the stent during its expansion. Once released into the lumen of the intestine, the stent progressively resumes its final diameter. It may be temporarily held in place by the hand of the surgeon clamping the stent via the walls of the intestine. The introducer sheath is then withdrawn. The sheath 3 unfolds spontaneously and progressively on withdrawal of the introducer sheath 4. This passes back through the anastomosis and then the anal orifice 10 in the rectrograde direction, totally releasing the sheath 3. After an average delay in the range four to six days, and because of the effect of intestinal contractions, the stent-sleeve assembly migrates progressively toward the anal orifice 10 from the upstream anchor site, which is sufficiently upstream of the anastomosis, preferably at least one meter from it in terms of intestine length, for the stent to reach the anal orifice five or six days later and only after resumption of intestinal transit, after which the device is eliminated with fecal matter, as represented in FIGS. 7A and 7B.

FIG. 8 represents an introducer sheath 4 including:
  a straight tubular external envelope $4_1$ made from a semi-rigid material so that it may be curved to follow the contours of the intestine when the introducer sheath is routed into the intestine from the anal orifice; the external envelope has an outside diameter that is 20 mm to 40 mm less than that of the wall of the intestine at the level of the anastomosis and an inside diameter and a length able to contain said anchor element 2 when compressed in the retracted configuration and said sheath deployed behind the anchor element, i.e. in practice a length in the range 100 mm to 150 mm;
  a buffer tube $4_4$ disposed axially inside said envelope and the distal end of which includes an abutment $4_5$ that abuts against said anchor element, which is itself immobilized by radial expansion at the distal end of the external envelope $4_1$; the buffer tube has a diameter slightly less than the inside diameter of the external envelope so as to contain the sheath 3 fixed to the downstream end of the anchor element, said sheath surrounding said buffer tube $4_1$; on withdrawal of the external envelope, the buffer tube retains the anchor element and therefore prevents withdrawal of the anchor element with the envelope and forces the anchor element out so as to be deployed radially against the wall of the intestine;

a flexible guide wire $4_2$ inserted on the axis of the buffer tube and the axis of said anchor element contained by the external envelope in the retracted configuration; the distal end of the guide wire is J-shaped to prevent trauma when it is inserted; it may be made of metal or synthetic material;

an atraumatic cone $4_3$ perforated axially to allow the guide wire $4_2$ to pass through it; the cone $4_3$ has a diameter that is greater than the inside diameter of the external envelope and is disposed downstream of the external envelope to facilitate routing the introducer sheath into the intestine.

The prosthesis is placed in the following manner:

1) The guide wire is inserted into the intestine as far as the anchor site of the anchor element.

2) The proximal end of the prosthesis is inserted externally of the anal orifice into the perforation of the atraumatic cone and then into the axial channel of the anchor element and then of the buffer tube on the axis of the introducer sheath.

3) The distal end of the external envelope of the introducer sheath is pushed along the guide wire inside the intestine, which pushes the atraumatic cone as far as the anchor site on the upstream side of the anastomosis.

4) The guide wire $4_2$ is withdrawn.

5) The external envelope $4_1$ is partially withdrawn, with the buffer tube $4_4$ held so that said anchor element is released.

6) The external envelope is withdrawn completely, together with the buffer tube and the atraumatic cone $4_3$.

According to the present invention, the device is used on an anastomosis as a preventive measure when there is no fistula. Nevertheless, the placement of the device 1 with the introducer sheath 4 includes maneuvers during its insertion that represent a potential hazard for the anastomosis in that they could injure it. A semi-rigid tube 8 called a protector tube is advantageously used to prevent this hazard.

The protector tube 8 temporarily protects the anastomosis during placement of the device, i.e. during insertion of the introducer sheath 4. The protector tube 8 is thus placed even before the introducer sheath 4 is placed and manipulated. Once the anastomosis has been produced, the protector tube is the first to be inserted.

This protector tube 8 is stiffer than the introducer sheath 4 and protects the intestinal wall so that the introducer sheath 4 does not deform the intestinal wall during its insertion.

The curved shape of the protector tube 8 enables it to espouse the curves of the intestine. The tube has a curved central part 8a similar to the curvature of the vertebral column at its lower end, which is referred to by the person skilled in the art as the sacral concavity curvature. Curvatures of this type are encountered in stapler devices. This tube 8 is open at both ends. The proximal end $8_4$ of the protector tube 8 is flared, enabling it to espouse the anatomical shape of the anal margin outside the external anal orifice. The same end includes on its external face a slightly inclined straight rod $8_5$ that is used to grasp the tube. The distal end of the tube 8 is not flared in order to be inserted into the anal orifice and then routed as far as a point upstream of the anastomosis 5. To this end, this non-flared end of the tube 8 is preferably reversibly blocked by an atraumatic cone $8_2$ mounted on a rod $8_3$ situated inside the lumen of the protector tube. This atraumatic cone $8_2$ prevents injury to the intestine during insertion of the protector tube 8.

The protector tube 8 has a length corresponding at least to the distance between the anal orifice and the anastomosis, i.e. in practice at least 5 cm to 25 cm, and an outside diameter less than or equal to that of the intestine at the level of the anastomosis, in practice the diameter of the stapler used to produce the anastomosis, i.e. in the range 10 mm to 40 mm, preferably in the range 20 mm to 30 mm. Its inside diameter is at least equal to that of the introducer sheath 4, to enable the introducer sheath to pass through it.

In practice, there are three types of anastomosis: colo-colic (colon to colon), colo-rectal (colon to rectum), and colo-anal (colon to anal passage). Depending on the type of anastomosis, the joining area between the two intestine ends is at a greater or lesser distance from the anal orifice (which on this occasion serves as a reference point). Accordingly, starting from the anal orifice and in the upstream direction, a colo-anal anastomosis is at a distance in the range 1 cm to 3 cm from the anal orifice, a colo-rectal anastomosis is at a distance in the range 4 cm to 10 cm, and a colo-colic anastomosis is at a distance in the range 11 cm to 20 cm from the anal orifice. This is why the length of the tube 8 is up to 25 cm, in order to be able to reach a colo-colic anastomosis, the type situated farthest from the anal orifice. For anastomoses nearer the anal orifice, not all the length of the tube need be introduced. The exact positioning of the tube 8 is always effected under the visual control of the operator.

Once the distal end of the protector tube has been routed to a point a few centimeters upstream of the anastomosis, the atraumatic cone is removed to free up the lumen of the protector tube. The introducer sheath 4 is then inserted into the lumen of the protector tube. The semi-rigid nature of the protector tube 8 protects the anastomosis 5 from rubbing by the introducer sheath 4. The farther the introducer sheath rises in the upstream intestine, the more it rubs on the walls of the intestine and the greater the pressure exerted by the operator on the introducer sheath. The lumen of the digestive tract has a non-negligible coefficient of resistance by virtue of its internal walls and even by virtue of the contractions of the intestine. This applies equally to withdrawing the introducer sheath 4.

In practice, once the anastomosis has been produced, the tube 8 with its atraumatic cone $8_2$ is picked up by the rod $8_3$ and the whole is introduced into the intestine via the anal orifice. The protector tube 8 is pushed through the anastomosis 5 into the upstream intestine 12. The distal end of the tube 8 is positioned at 8 and the rod $8_3$ comes into contact with the anal margin; they are held in place by the hand of the operator. The atraumatic cone $8_2$, the diameter of which is slightly less than that of the tube 8, is withdrawn. The introducer sheath 4 is inserted through the flared orifice $8_4$ of the protector tube 8 in order to push it through the protector tube. The subsequent steps unfold as described above in relation to the use of the introducer sheath 4. All maneuvers effected during manipulation of the introducer sheath 4 are effected via the protector tube 8, which provides a protective barrier for the anastomosis and prevents it being injured. After complete withdrawal of the introducer sheath 4 the protector tube is withdrawn in turn.

The appropriately shaped end 2b of the stent 2 facilitates its progress in the intestinal lumen. Nevertheless, the anastomosis region often features a stenosis at the level of the junction between the two intestine ends and thus has a diameter less than the intestine on either side. This is caused by healing of the anastomosis. This stenosis may potentially impede the progress of the stent 2 through the anastomosis 5 and in the extreme situation cause closing of the stent in this area. Migration of the stent may always be facilitated by maneuvers exerting traction on the proximal part of the sheath 3, but this is sometimes not sufficient. Assistance may then be provided by a protector tube 8, which facilitates the passage of the stent or in the extreme situation enables re-opening of the stent.

It is a semi-rigid cylindrical tube that has the same curvature as the sacral concavity and the intestine, like the protector tube 8 described above, but extending from the anal orifice as far as the upstream side of the anastomosis 5. One of its ends, referred to as the proximal end, is flared to adapt to the conformation of the anal margin. However, its inside diameter is greater than that of the anchor element or stent at least in the radially retracted configuration. Its length is identical to that of the protector tube for placing the introducer sheath 4.

The maneuver entails identifying the anastomosis area under radioscopic control. This area is easily found by virtue of the presence of the clips that were used to effect the anastomosis and the presence of the stent, which carries radio-opaque markings.

When the downstream end of the sheath arrives downstream of the anastomosis 5, the downstream end of the sheath 3 is inserted into the lumen of the tube 8 via its distal end. The sheath is brought out via the proximal end of the protector tube. The protector tube 8 slides progressively along the sheath 3, which serves as a guide wire for it. It enters the anal passage and then the intestine. The operator pushes it into contact with the downstream end of the stent, where it is immobilized. The downstream end of the sheath is pulled progressively. The upstream end of the sheath attached to the stent enters the lumen of the distal end of the tube. Traction continues to be applied to the downstream end of the sheath. The downstream end of the stent follows the upstream end of the sheath. The retraction properties of the stent enable it to adopt the inside diameter of the tube and to enter the lumen at the distal end of the tube, the diameter of which is at least equal to that of the introducer sheath. Continuous traction on the downstream sheath enables the stent to enter the tube 8 entirely. The whole of the tube 8 containing the stent and the sheath is then withdrawn via the anal passage.

FIG. 11 represents a preferred version of a device of the invention in which the sheath 3 covers the stent 2 only partly, covering all its conical downstream end, the connection between the sheath 3 and the stent 2 beginning upstream of the conical end over an area 2*c* that has a length in the range approximately 3 mm to 30 mm, preferably in the range 5 mm to 15 mm, upstream of the upstream end of the appropriately shaped area 2*b*.

The stent 2, which is made in the form of a spiral wire mesh, has a silicone coating 24 that is thinner than said sheath and confers on said stent greater radial and longitudinal deformability than said sheath. Thus if the stent is immobilized upstream of the anastomosis, preventing it from deploying and/or migrating through the anastomosis, manual traction may be exerted on the proximal end of said sheath, deforming it by reducing its diameter and stretching the rest of the stent to facilitate its passage through the anastomosis.

The stent 2 preferably has at each end a thread-like extension known as a lasso approximately 10 mm long, preferably made from the same material as the stent. As known in the art, traction on the lasso at the downstream end of the stent then makes it possible to facilitate reducing the diameter of the stent and stretching the stent axially using a commercially available instrument of the colonoscope or rectoscope type.

In contrast, and again in known manner, traction on the lasso at the upstream end of the stent makes it possible, in the event of jamming of the stent, to turn the stent inside out by pulling its upstream end $2_1$ inside itself in the upstream to downstream direction so as to free it from the intestinal wall, in which it may have become incorporated.

In known manner, the thread-like end $2_3$ of the stent, called the lasso, extends from the periphery of the downstream end $2_2$ or the upstream end $2_1$ of said stent.

In another embodiment, as well as or instead of the thread-like downstream end called the lasso described above, a flexible strand with the same characteristics as the lasso is attached to the proximal (downstream) end of the stent, around its periphery, and threaded through the mesh. Thus traction on this strand leads to almost complete closure of the proximal downstream end of the stent at which the sheath begins. This strand extends inside said sheath as far as its proximal end situated at the anus, so that access to said strand does not necessarily require the use of a colonoscope or rectoscope. In the event of incorporation of the stent, closing the proximal end of the stent by pulling on the strand helps to facilitate passage of the stent through the anastomosis.

The invention claimed is:

1. A surgical device for temporary protection of an anastomosis in the colon, the rectum, or the anal passage, the device including:
   a) a semi-rigid hollow longitudinal temporary anchor element, a first wall of which defines a surface of revolution about a longitudinal axis, including a substantially cylindrical main portion with a substantially circular section, and said first wall having an outside diameter that may be varied in a controlled manner between:
      a reduced outside diameter of, at most, 10 mm in a radially retracted configuration of said first wall; and
      a maximum outside diameter in a maximum radial expansion configuration of the cylindrical main portion of said first wall in the range 20 mm to 40 mm;
      said maximum outside diameter of the anchor element being higher or equal to that of said wall intestine in the colon, at rest, in the absence of intestinal transit, and lower than the dilated maximum diameter of the wall intestine in the colon upon resumption of the intestinal transit so that said anchor element is capable of remaining temporarily fixed to the wall intestine in the colon for at least three days in the absence of intestinal transit by the only virtue of a radial expansion force of the anchor element against the intestinal wall, said anchor element not comprising other fixing means than said radial expansion force capable of fixing the anchor element to the wall intestine, and the anchor element is capable of being released and migrate by sliding in contact with the wall intestine upon resumption of the intestinal transit; and
   b) a sheath having a flexible tubular wall permanently fixed against said first wall of said anchor element;
   wherein:
   1) said first wall of said temporary anchor element includes said cylindrical main portion of said first wall having a length of at least 50 mm; and
   2) said sheath has, when at rest, a length downstream of said anchor element of at least 50 cm, and an outside diameter in the range 20 mm to 40 mm, and is made from a biocompatible elastomer material having a wall thickness in the range 0.05 mm to 1 mm;
   wherein the length of the sheath is such that the anchor element is able to migrate for at least three days from an anchor site of the anchor element in the colon on resumption of transit while the sheath covers the anastomosis.

2. A device according to claim 1, wherein said cylindrical main portion of said first wall extends from an upstream longitudinal end of said first wall as far as an appropriately shaped downstream end portion having a smaller diameter than the cylindrical main portion, the outside diameter of the downstream end of said first wall in the maximum radial expansion configuration being in the range 20 mm to 35 mm, and the length of said appropriately shaped downstream end portion of the first wall being in the range 10 mm to 30 mm, the diameter of said downstream end portion decreasing progressively between said main portion and said downstream end of said first wall, to facilitate the migration of the anchor element through a stenosis of the anastomosis area of reduced diameter.

3. A device according to claim 2, wherein the diameter of said appropriately shaped downstream end portion is reduced by surrounding it with an elastomer material ring having a diameter less than said diameter of said main portion in said maximum radial expansion configuration.

4. A device according to claim 2, wherein a connection between said sheath and said anchor element is produced by virtue of said sheath covering at least an external surface of said downstream end portion of said anchor element.

5. A device according to claim 4, wherein said anchor element is a stent-type enteral prosthesis covered with a coating of silicone or polyurethane type elastomer synthetic material, said coating being more flexible than the elastomer material of said sheath, and the connection between said sheath and said anchor element being produced by virtue of said sheath covering said anchor element over only part of the length of said anchor element including at least said appropriately shaped downstream end of progressively reducing diameter.

6. A device according to claim 1, wherein:
said anchor element is made from a material conferring on it radial elasticity properties such that it may be compressed radially in said retracted configuration and adopt said maximum radial expansion configuration after the radial compression is released; and
said biocompatible elastomer of said sheath is an elastomer-based biocompatible polymer material of silicone or polyurethane type having said wall thickness in the range 0.1 mm to 0.5 mm and having radial and longitudinal elasticity properties, shape memory properties, and non-stick properties.

7. A device according to claim 6, wherein said temporary anchor element is a stent-type enteral prosthesis said first wall of which is formed by a spiral elastomer or metal wire mesh.

8. A device according to claim 1, wherein said sheath is made from said elastomer-based biocompatible polymer material having the following properties:
a Shore A hardness in the range 5 to 95;
a degree of remanent deformation on compression (RDC) in the range 10% to 35%; and
a coefficient of friction in the range 0.30 to 0.90; and
wherein said sheath presents radical and longitudinal elasticity properties similar to, or greater than, those of the wall of the colon, and presents shape memory properties enabling the sheath to return naturally to an original shape of the sheath after the sheath is deformed by bending.

9. An insulation assembly of a device according to claim 1, further comprising an introducer sheath including:
a tubular external envelope that is adapted to contain said anchor element when compressed in said retracted configuration, and to retain said anchor element inside the distal end of said external envelope, and is sufficiently long to contain said sheath, said external envelope having a length of at least 110 cm; and
means for routing the distal end of said introducer sheath from an anal orifice to said anchor site in an intestine upstream of the anastomosis.

10. An insulation assembly according to claim 9, further comprising a protector tube that includes a portion of curved shape conforming to the curvature of a sacral concavity, is stiffer than said tubular external envelope of the introducer sheath, has an outside diameter and length such that said protector tube may be introduced via the anal orifice and extend between the anal orifice and a point upstream of said anastomosis, and has an inside diameter and a curvature conforming to the curvature of the sacral concavity such that said protector tube is able to contain said introducer sheath and route it between the anal orifice and said anastomosis.

11. An insulation assembly according to claim 9, further comprising a means for disengaging said anchor element from the external envelope in the form of a buffer tube including an abutment at its distal end in contact with the longitudinal end of said anchor element, said sheath downstream of the anchor element surrounding said buffer tube inside said external envelope.

* * * * *